United States Patent [19]

Kulick

[11] Patent Number: 4,571,180
[45] Date of Patent: Feb. 18, 1986

[54] DENTAL INSTRUMENT

[76] Inventor: Walter K. Kulick, 11140 NW. 26th St., Sunrise, Fla. 33322

[21] Appl. No.: 587,459

[22] Filed: Mar. 8, 1984

[51] Int. Cl.⁴ .............................................. A61C 19/04
[52] U.S. Cl. ...................................... 433/72; 433/102
[58] Field of Search ................. 433/102, 72, 229, 224, 433/75; 33/174 D, 174 R; 128/774

[56] References Cited

U.S. PATENT DOCUMENTS

| | | | |
|---|---|---|---|
| 1,417,237 | 5/1922 | Evans | 433/75 |
| 2,181,746 | 11/1939 | Siebrandt | 128/305.1 |
| 3,213,541 | 10/1965 | Raffman | 33/143 |
| 3,330,040 | 6/1967 | Kahn | 433/102 |
| 3,772,791 | 11/1973 | Malmin | 433/224 |
| 3,993,045 | 11/1976 | Ion | 128/774 |
| 4,165,562 | 8/1979 | Sarfatti | 433/102 |
| 4,462,802 | 7/1984 | Sekiya | 433/102 |

Primary Examiner—John J. Wilson
Attorney, Agent, or Firm—Saidman, Sterne, Kessler & Goldstein

[57] ABSTRACT

A dental instrument is attachable to a tooth whose apex is to be located. Indicator means, composed of a material that produces a visible image on a radiograph, is adjustably coupled to the mounting means to permit adjustment of the indicator means relative to the mounting means. When the dental instrument is attached to the tooth, the indicator means is adjusted relative to the tooth to permit substantial alignment of the images of the indicator means and tooth apex on the radiograph.

8 Claims, 2 Drawing Figures

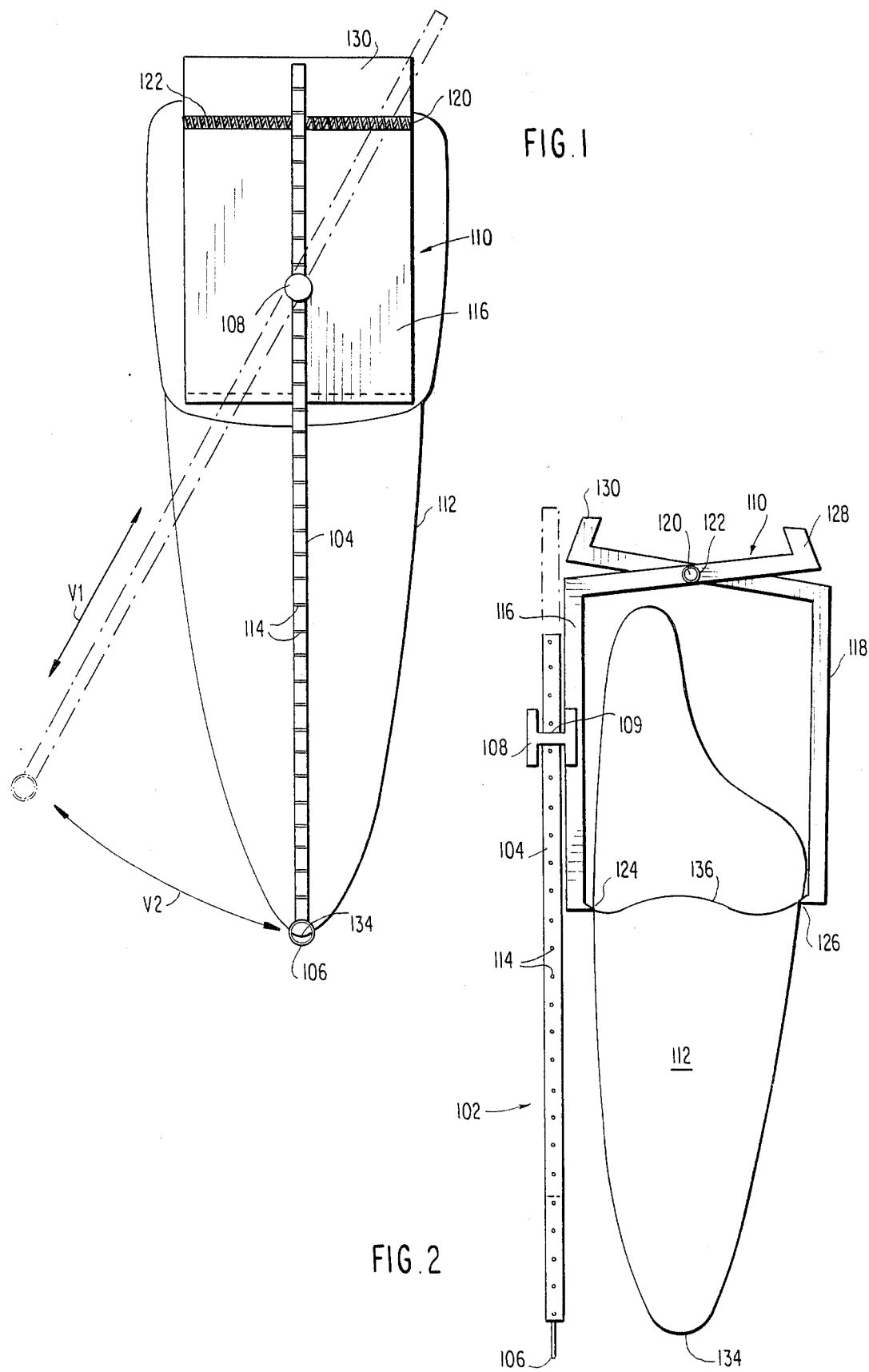

DENTAL INSTRUMENT

BACKGROUND OF THE INVENTION

1. Field of Use

The present invention relates to the dental procedure of apicoectomy.

2. Description of the Related Art

An apicoectomy is a procedure used in dentistry in which the apex of a tooth is exposed surgically, the apex resected, and the area curretted. The procedure has been used for decades, perhaps even centuries, to provide relief from dental disease. A diseased tooth irritates the bone surrounding its root, causing pain and damage to the bone. An apicoectomy promotes healing of the bone and provides relief from pain by removal of the diseased apex of the tooth, which is typically the foremost cause of irritation.

Traditionally, the location of the apex has been determined in a variety of ways, none of which have proved to be very exact. In fact, the inexactitude of this determination is the primary factor in limiting the use of the procedure to cases where other treatments have not been successful. In the past, the operation has involved a high degree of risk of permanent nerve damage. The mandibular nerve is very close to the apices of the teeth in the mandible. To reach the diseased apex, a dentist must drill through the mandible. Typically, he makes an incision in the gum, reflects the tissue to expose the jaw bone and drills exploratory holes in the bone until he finds the apex of the tooth. Pieces of bone are then removed until the diseased area is found and entirely exposed. The more exact the initial approximation of the location of the apex, the less risk there is of drilling into the mandibular nerve and causing paresthesia. For years, dentists have sought a means of reducing the guesswork involved in determining the location of the apex.

One procedure which was developed is described in U.S. Pat. No. 1,417,237 to Evans. A probe is entered through the root canal of a diseased tooth to the point of emergence just beyond the root apex. The depth of the probe is measured by an external guide, so that a drill, directed by the guide from the exterior of the jaw, may be caused to penetrate the bone at right angles to the probe at the point where the latter has located the root apex.

An alternative method was later developed in which the physical guide structure of the Evans device was eliminated. U.S. Pat. No. 3,772,791 to Malmin discloses a system to measure the depth of the root canal by insertion of a probe into the root canal of the tooth. A measurement sleeve is secured to the probe and marked with indications of length so that the depth of the probe may be accurately determined by x-ray.

The Evans and Malmin patents both disclose instruments having probes which are inserted into the root canal of a tooth. The Evans device has an inflexible probe which is useful only in cases in which the diseased tooth has a straight, clear root canal. Any curvature of the root canal would prevent proper insertion of the probe. Therefore, in many such cases, the instrument would be useless. The Malmin device may successfully determine the length of even a curved root canal in preparation for root treatment, but it provides no guide for locating the apex of a tooth for surgical procedures. Neither device may be used on a tooth having a calcified root canal or on a tooth which has been previously treated and the root canal filled. In these circumstances, the root canal is blocked or filled so as to prevent the insertion of a probe.

Moreover, the risk of inexactitude still exists with the Malmin and Evans techniques. Both devices determine the depth of the root canal but neither provides an exact indication of where the dentist should drill to find the apex. The Evans device provides an external drill guide, but the guide is only accurate on a tooth having a straight root canal, and is useless if the root canal is calcified or previously treated. The Malmin device allows an x-ray to show the location of the apex, but provides no guide for drilling nor any means of measuring the position of the apex other than by its depth. The device is suitable for determining the length of the root canal prior to treatment, but is not suitable for surgical procedures.

The present invention eliminates the need for a straight, clear root canal by locating the apex of the tooth with an external guide and measuring device. Because of the two-dimensional freedom of the guide, the location of the apex is determined to a greater certainty than is possible simply by determining its depth. The procedure described below, made possible by the present invention, permits the dentist to locate the exact apex of a tooth without removing any bone, and consequently, without a high degree of risk of nerve damage. The procedure is also applicable to filled or calcified teeth because it is not necessary to insert a probe into the root canal of a diseased tooth.

SUMMARY OF THE INVENTION

The dental instrument of the present invention includes mounting means for mounting the dental instrument to a tooth whose apex is to be located, indicator means composed of a material that produces a visible image on a radiograph, and coupling means for adjustably coupling the indicator means to the mounting means such that images of the indicator means and the tooth apex may be substantially aligned on the radiograph.

In a preferred embodiment, the indicator means is an elongated rod-like member composed of a material that is substantially transparnt to x-rays. A plurality of wire segments are spaced along the length of the rod-like member. The rod-like member is terminated by a wire loop, imagable upon a radiograph, through which a drill or other marking device may be passed when the wire loop is properly aligned with the tooth apex. The indicator is mounted to move relative to the coupling means in the direction of the longitudinal axis of the rod-like member and rotatably about a pivot axis extending through the coupling means. The mounting means comprises two arms hinged together and biased towards each other to maintain a firm grip upon the surface of the tooth. The coupling means is pivotably connected to one of the arms of the mounting means.

BRIEF DESCRIPTION OF THE DRAWINGS

FIG. 1 is a front view of the preferred embodiment of the dental instrument of the present invention; and FIG. 2 is a side view of the dental instrument illustrated in FIG. 1.

DETAILED DESCRIPTION OF THE PREFERRED EMBODIMENT

Referring to FIGS. 1 and 2, the dental instrument, generally designated 102, comprises a rod 104 terminated by a wire loop 106. The rod 104 is adjustably attached by a connector 108 to a retaining clip 110 for securing the dental instrument 102 to a tooth 112. Preferably, the rod is made of a known plastic, but other materials that are transparent or essentially so to x-rays may be used. Wire segments 114 of a length equal to the width of the rod 104 are imbedded in the rod 104 every one millimeter along its length, or at any other regular spacing such that the wire segments 114 may be used as a measuring scale and as a means of checking for radiographic distortion of an x-ray.

The wire loop 106 and wire segments 114 are composed of a material that produces a visible image on a radiograph and are of sufficient thickness to be clearly distinguishable on a radiograph of the tooth 112 with the dental instrument 102 attached. The wire loop 106 is of a sufficient inside diameter to permit passage therethrough of a dental device to mark where drilling is to be done. The mark may be made by a drill or other device suitable to the purpose. The instrument 102 is removed prior to drilling after the location for drilling is determined and marked. The wire loop 106 and wire segments 114 are positioned in a plane substantially parallel to the surface of the tooth 112 such that a radiographic image of the tooth 112, exposed by x-rays emanating from a source external to the mouth of the patient, will have superimposed on it an image of the wire loop 106 and wire segments 114, similar to the front view shown in FIG. 1.

The retaining clip 110 comprises an inner arm 116 and an outer arm 118 fastened together in a hinge-like manner. The inner arm 116 and outer arm 118 may abut one another at a hinge pin 120 in a manner similar to the joining of the arms of a scissor. A spring 122 substantially surrounds at least a portion of the hinge pin 120 and is configured to apply a resilient force to the arms of the retaining clip 110 tending to keep tips 124 and 126 of the arms 116 and 118, respectively, pressed against the surface of the tooth absent the application of a compressing force upon handle portions 128 and 130 of arms 116 and 118, respectively. Alternatively, the handles 128, 130 and hinge pin 120 may be divided into fingers so that when the arms are joined together, the fingers of one arm are free to pass between the fingers of the other.

The rod 104 is joined to the inner arm 116 of the retaining clip 110 by connector 108. The connector 108 permits movement of the rod 104 in a plane substantially parallel to the surface of the tooth 112 and the surface of the inner arm 116. The rod 104 is free to slide along its length in a manner indicated by the sliding vector V1 and to rotate about the connector 108 as indicated by the rotational vector V2.

The connector 108 is fixed in position relative to the retaining clip 110. Connector 108 may be a simple post or pivot passing through the inner arm 116 of the retaining clip 110 with a channel 109 cut through the portion of the connector 108 which protrudes from the external surface of the inner arm 116. The rod 104 is inserted through the channel 109 which is dimensioned so that a snug fit is achieved between the rod 104 and the connector 108. Preferably and advantageously, the snugness of the fit between the rod 104 and the connector 108 and of that between the connector 108 and the inner arm 116 will allow manual adjustment of the position of the rod 104 relative to the retaining clip 110 while constraining further motion once the proper positioning is achieved.

The drawing depicts the tooth 112 having an apex 134 and a gum line 136. Preferably and advantageously, the tips 124 and 126 of the inner arm 116 and outer arm 118, respectively, protrude inwardly toward the tooth 112, forming a sharp ridge at the point of contact with the tooth 112 to concentrate the force exerted by the spring 122 and to thereby provide a stronger grip on the tooth 112. The arms of the instrument are preferably of a length such that the tips 124 and 126 may reach the gum line 136 of the tooth where the surface of the tooth is broad and flat.

FIG. 1 shows the dental instrument 102 clipped to a tooth 112. The tips 124, 126 of the arms 116, 118 of the instrument meet the broad and flat surface of the tooth 112 just above the gum line 136. The dental instrument is oriented such that the rod 104 is interposed between the tooth 112 and a source of x-rays external to the mouth of the patient. The dentist adjusts the position to the wire loop 106 to an approximate location of the apex 134 by moving the rod 104 along the directions indicated by the sliding vector V1 and the rotational vector V2. A radiograph is taken with the instrument in place. The x-ray will yield a picture of the tooth 112 with the loop and instrument superimposed somewhere around the apex 134. If the loop 106 is not close enough to the apex 134 to allow the dentist to proceed safely with the surgery, the instrument is adjusted using the x-ray as a guide and the process is repeated until, preferably and advantageously, the loop 106 is positioned over the exact apex 134 of the tooth as shown in FIG. 1. The dentist is then able to accurately drill through the jaw bone to the apex 134 by drilling in the area determined by the position of the wire loop 106 and marked prior to removal of instrument 102. The wire segments 114 inserted at a regular spacing along the length of the rod 104 will appear superimposed on the radiographic image of the tooth and may be used by the radiograph operator to determine if any radiographic distortion occurred in the x-ray.

It may be further appreciated that the instrument 102 may be used to locate an object such as a tumor or foreign body within the bone of the maxilla or the mandible. The instrument would benefit the surgeon in locating the object prior to surgery.

Obviously, numerous modifications and variations of the present invention are possible in light of the above teachings. It is therefore to be understood that within the scope of the appended claims, the invention may be practiced otherwise than as specifically described herein.

What is claimed is:

1. A dental instrument for locating the apex of a tooth in a non-invasive manner comprising:
    mounting means for mounting the dental instrument to a tooth whose apex is to be located, said mounting means including means for attaching said instrument to the external surface of a tooth in a non-invasive manner;
    indicator means comprising a material that produces a visible image on a radiograph; and
    coupling means for adjustably coupling the indicator means to the mounting means to permit adjustment of the indicator means relative to the mounting means;

wherein, when the dental instrument is mounted to the tooth, the indicator means is located external to the tooth and is adjustable relative to the tooth to permit substantial alignment of the images of the indicator means and tooth apex on the radiograph.

2. A dental instrument according to claim 1, wherein said indicator means comprises an elongated member having means fixed at regular intervals therealong which are of a material that produces a visible image on a radiograph.

3. A dental instrument for locating the apex of a tooth comprising:
mounting means for mounting the dental instrument to a tooth whose apex is to be located;
indicator means comprising a rod-like member composed of a material that is substantially transparent to x-rays and a plurality of wire segments of a material that produces a visible image on a radiograph spaced at regular intervals along said rod-like member, the wire segments having their longitudinal axes aligned substantially transverse to the longitudinal axis of the rod-like member; and
coupling means for adjustably coupling the indicator means to the mounting means to permit adjustment of the indicator means relative to the mounting means;
wherein, when the dental instrument is mounted to the tooth, the indicator means is located external to the tooth and is adjustable relative to the tooth to permit substantial alignment of the images of the indicator means and tooth apex on the radiograph.

4. A dental instrument according to claim 3, wherein said indicator means further comprises a wire loop located at the end portion of the rod-like member and composed of a material that produces a visible image on a radiograph.

5. A dental instrument according to claim 4, wherein the rod-like member engages the coupling means and is movable relative to the coupling means in the direction of the longitudinal axis of the rod-like member and rotatably about a pivot axis extending through the coupling means.

6. A dental instrument acording to claim 5, wherein the wire loop is located at the end portion of the rod-like member remote from its engagement with the coupling means; and wherein the wire loop is of sufficient diameter to permit passage therethrough of a dental marking device and its image on the radiograph substantially encircles the apex of the tooth when the indicating means is properly aligned with the tooth apex.

7. A dental instrument for locating the apex of a tooth comprising:
mounting means for mounting the dental instrument to a tooth whose apex is to be located, said mounting means comprising:
two arms, each at least as long as the length of a tooth from the gum line to the crown, and each having an inwardly protruding ridge for gripping the surface of the tooth,
hinge means connecting the two arms together such that a portion of each arm extends above the hinge means to provide a surface for grasping the instrument, and
bias means surrounding a portion of the hinge means to bias the arm towards each other;
indicator means comprising a material that produces a visible image on a radiograph; and
coupling means for adjustably coupling the indicator means to the mounting means to permit adjustment of of the indicator means relative to the mounting means;
wherein, when the dental instrument is mounted to the tooth, the indicator means is located external to the tooth and is adjustable relative to the tooth to permit substantial alignment of the images of the indicator means and tooth apex on the radiograph.

8. A dental instrument according to claim 7, wherein:
said indicator means comprises a rod-like member composed of a material that is substantially transparent to x-rays, and a plurality of wire segments fixed at regular intervals along the rod-like member and composed of a material that produces a visible image on a radiograph; and
said coupling means comprises a connector member pivotably mounted to one of said arms, and said rod-like member engages the connector member in such a way as to permit movement of the rod-like member relative to the connector member in the direction of the longitudinal axis of the rod-like member and rotatably about the pivot axis defined by the mounting of the connector member to said one arm.

* * * * *